United States Patent [19]

Kasuga et al.

[11] Patent Number: 5,066,619

[45] Date of Patent: Nov. 19, 1991

[54] GLASS-CERAMICS, PROCESS OF PRODUCING THE GLASS-CERAMICS AND DENTAL CROWN USING THE GLASS-CERAMICS

[75] Inventors: Tomoko Kasuga; Toshihiro Kasuga, both of Akishima, Japan

[73] Assignee: Hoya Corporation, Tokyo, Japan

[21] Appl. No.: 571,209

[22] Filed: Aug. 23, 1990

[30] Foreign Application Priority Data

Sep. 5, 1989 [JP] Japan .................................... 1-229803

[51] Int. Cl.$^5$ .............................................. C03C 10/16
[52] U.S. Cl. .......................................... 501/3; 106/35
[58] Field of Search ............................. 501/3; 106/35

[56] References Cited

U.S. PATENT DOCUMENTS

| | | | |
|---|---|---|---|
| 3,689,293 | 9/1972 | Beall ....................................... | 501/3 |
| 4,118,237 | 10/1978 | Beall et al. ............................... | 501/3 |
| 4,431,420 | 2/1984 | Adair ....................................... | 501/3 |
| 4,747,876 | 5/1988 | Hakematsuka et al. ................ | 501/3 |
| 4,789,649 | 12/1988 | Abert et al. ............................. | 501/3 |
| 4,799,887 | 1/1989 | Hakematsuka et al. ................ | 501/3 |

FOREIGN PATENT DOCUMENTS 0132332  9/1978  German Democratic Rep. ..... 501/3

*Primary Examiner*—Mark L. Bell
*Attorney, Agent, or Firm*—Nixon & Vanderhye

[57] ABSTRACT

Disclosed is glass-ceramics produced by and a method of producing the glass-ceramics comprising the step of precipitating a calcium-potassium mica crystal consisting of Ca-K-Mg-Al-Si-O-F and at least one crystal selected from the group consisting of an enstatite crystal, an akermanite crystal and a diopside crystal, from glass containing components, in percent by weight, 2 to 17% of CaO, 0.5 to 5% of $K_2O$, 20 to 35% of MgO, 30 to 50% of $SiO_2$, 5 to 30% of $Al_2O_3$, and 1.5 to 14% of Fluorine (Calculated as F); or precipitating a calcium-potassium-sodium mica crystal consisting of Ca-K-Na-Mg-Al-Si-O-F and at least one crystal selected from the group consisting of an enstatite crystal, an akermanite crystal, a diopside crystal, an anorthite crystal and a richterite crystal, from glass containing components, in percent by weight, 2 to 17% of CaO, 0.5 to 5% of $K_xO$, 0.1 to 4% of $Na_2O$, 15 to 35% of MgO, 30 to 49% of $SiO_2$, 5 to 30% of $Al_2O_3$, and 1.5 to 14% of Fluorine (calculated as F). In the above method, the glass is heat treated successively at a temperature higher than its glass transition point by a range of from 10° to 100° C. and at a temperature higher than its glass transition point by a range of from 100° to 500° C. to thereby precipitate the above-mentioned matters.

Further disclosed is an artificial dental crown composed of the above-mentioned glass-ceramics.

9 Claims, No Drawings

GLASS-CERAMICS, PROCESS OF PRODUCING THE GLASS-CERAMICS AND DENTAL CROWN USING THE GLASS-CERAMICS

BACKGROUND OF THE INVENTION

1. Field of the Invention

The present invention relates to glass-ceramics having a desired hardness and being excellent in mechanical strength and machinability. Further, the present invention relates to a process for producing glass-ceramics having a desired hardness and being excellent in mechanical strength, machinability and light transmission property.

Further, the present invention relates to glass-ceramics having a desired hardness and being excellent in mechanical strength, machinability and chemical durability. Further, the present invention relates to a process for producing glass-ceramics having a desired hardness and being excellent in mechanical strength, machinability, chemical durability and light transmission property.

These kinds of glass-ceramics are useful as materials for an artificial dental crown and mold materials (mold materials for producing plastic articles, mold materials for producing ophthalmic lenses, and the like).

2. Description of the Prior Art

In recent years, machinable ceramics produced by precipitating a mica crystal have been used as a ceramic material, such as a material for a dental crown, more beautiful and more excellent in biocompatibility than a metal material.

For example, ceramics produced by precipitating mica tetrasilicofluoride ($KMg_{2.5}Si_4O_{10}F_2$) from glass mainly containing $SiO_2$, $MgO$, $MgF_2$, $K_2O$, $ZrO_2$ and $Al_2O_3$ have been described in Japanese Patent Unexamined Publication No. Sho-59-50046 (hereinafter referred to as "Prior Art 1").

The ceramics are provided to improve stain resistance through addition of a small quantity of $Al_2O_3$ or $ZrO_2$.

Further, ceramics improved in mechanical strength, produced by precipitating mica ($Na.Mg_3.(Si_3AlO_{10})F_2$), $\beta$-eucryptite ($Li_2O.Al_2O_3.2SiO_2$) and $\beta$-spodumene ($Li_2O.Al_2O_3.4SiO_2$) from glass mainly containing $SiO_2$, $MgO$, $Na_2O$, $Li_2O$, $ZrO_2$, $TiO_2$, $Al_2O_3$ and fluorine have been described in Japanese Patent Unexamined Publication No. Sho-62-70244 (hereinafter referred to as "Prior Art 2").

On the other hand, crystallized glass produced by precipitating potassium fluoro-richterite glass containing components being present within the ranges: 50 to 70% by weight of $SiO_2$, 4 to 15% by weight of CaO, 8 to 25% by weight of MgO, 2 to 9% by weight of $Na_2O$ and 2 to 12% by weight of $K_2O$ has been disclosed in Japanese Patent Unexamined Publication No. Sho-59-207850 (hereinafter referred to as "Prior Art 3"). According to the Prior Art 3, a metastable-phase mica crystal is formed in a temperature range from 600° to 800° C. before precipitation of potassium fluoro-richterite, and then potassium fluoro-richterite is formed by heating the metastable-phase mica crystal to a temperature not lower than 800° C.

However, the bending strength of the machinable ceramics described in the Prior Art 1 (Japanese Patent Unexamined Publication No. Sho-59-50046) is about 1500 kg/cm². There arises a problem in that cutting a tooth portion by 1 mm or more is required for securing strength in the case where the machinable ceramics are used as an artificial dental crown. Accordingly, the portions where the ceramics can be used are restricted within narrow scopes. Further, because the ceramics are not sufficient in bending strength, sufficient care must be taken at the time of producing or mounting of an artificial dental crown, compared with the case of a metal material.

The bending strength of the machinable ceramics in the Prior Art 2 (Japanese Patent Unexamined Publication No. Sho-62-70244) is about 2200 kg/cm², which is higher than that of the machinable ceramics in the Prior Art 1. However, the ceramics have a disadvantage in that the hardness of the ceramics is more than that of a natural tooth. Accordingly, in the case where the machinable ceramics are used as an artificial dental crown, a problem arises in that the natural tooth is rather worn out because the artificial crown is harder than the natural tooth.

The glass-ceramics described in the Prior Art 3 (Japanese Patent Unexamined Publication No. Sho-52-207850) have a disadvantage in that it is difficult to precipitate stably a mica crystal from the glass composition defined in the Prior Art 3 because the mica crystal is precipitated as a metastable phase. This is because glass containing a large amount (50 to 70% by weight) of $SiO_2$ in the Prior Art 3 is stabilized at the time of crystallization to thereby make it difficult to precipitate a large amount of fine mica crystal.

Further, in the case where the glass-ceramics are used as a dental crown, the crown is left for a long time in the oral cavity being present under a severe condition. Accordingly, materials excellent in both mechanical strength and chemical durability have been desired.

Further, from the point of view of beauty or the like, materials having light transmission property have been desired.

SUMMARY OF THE INVENTION

A first object of the present invention is therefore to provide glass-ceramics having a desired hardness, being excellent in both mechanical strength and machinability and being suitable for an artificial dental crown.

A second object of the invention is to provide a process of producing glass-ceramics having a desired hardness, being excellent in mechanical strength, machinability and light transmission property and being suitable for an artificial dental crown.

A third object of the invention is to provide glass-ceramics having a desired hardness, being excellent in mechanical strength, machinability and chemical durability and being suitable for an artificial dental crown.

A fourth object of the invention is to provide a process of producing glass-ceramics having a desired hardness, being excellent in mechanical strength, machinability, light transmission property and chemical durability and being suitable for an artificial dental crown.

The first object of the invention is attained by glass-ceramics produced by precipitating from glass a calcium-potassium mica crystal consisting of Ca—K—Mg—Al—Si—O—F and at least one crystal selected from the group consisting of an enstatite crystal, an akermanite crystal and a diopside crystal, the glass containing components being present within the ranges:

| | Percent by weight |
|---|---|
| CaO | 2 to 17 |

-continued

|  | Percent by weight |
| --- | --- |
| $K_2O$ | 0.5 to 5 |
| MgO | 20 to 35 |
| $SiO_2$ | 30 to 50 |
| $Al_2O_3$ | 5 to 30 |
| Fluorine (calculated as F) | 1.5 to 14 |

The second object of the invention is attained by a process of producing glass-ceramics comprising heating glass containing components being present within the ranges:

|  | Percent by weight |
| --- | --- |
| CaO | 2 to 17 |
| $K_2O$ | 0.5 to 5 |
| MgO | 20 to 35 |
| $SiO_2$ | 30 to 50 |
| $Al_2O_3$ | 5 to 30 |
| Fluorine (calculated as F) | 1.5 to 14 | successively at a temperature higher than its glass transition point by a range of from 10° to 100° C. and at a temperature higher than its glass transition point by a range of from 100° to to 500° C., to thereby precipitate from the glass a calcium-potassium mica crystal consisting of Ca—K—Mg—Al—Si—O—F and at least one crystal selected from the group consisting of an enstatite crystal, an akermanite crystal and a diopside crystal.

The third object of the invention is attained by glass-ceramics produced by precipitating from glass a calcium-potassium-sodium mica crystal consisting of Ca—K—Na—Mg—Al—Si—O—F and at least one crystal selected from the group consisting of an enstatite crystal, an akermanite crystal, a diopside crystal, an anorthite crystal and a richterite crystal, the glass containing components being present within the ranges:

|  | Percent by weight |
| --- | --- |
| CaO | 2 to 17 |
| $K_2O$ | 0.5 to 5 |
| $Na_2O$ | 0.1 to 4 |
| MgO | 20 to 35 |
| $SiO_2$ | 30 to 49 |
| $Al_2O_3$ | 5 to 30 |
| Fluorine (calculated as F) | 1.5 to 14 |

The fourth object of the invention is attained by a process of producing glass-ceramics comprising heating glass containing components being present within the ranges:

|  | Percent by weight |
| --- | --- |
| CaO | 2 to 17 |
| $K_2O$ | 0.5 to 5 |
| $Na_2O$ | 0.1 to 4 |
| MgO | 20 to 35 |
| $SiO_2$ | 30 to 49 |
| $Al_2O_3$ | 5 to 30 |
| Fluorine (calculated as F) | 1.5 to 14 | successively at a temperature higher than its glass transition point by a range of from 10° to 100° C. and at a temperature higher than its glass transition point by a range of from 100° to 500° C., to thereby precipitate from the glass a calcium-potassium-sodium mica crystal consisting of Ca—K—Na—Mg—Al—Si—O—F and at least one crystal selected from the group consisting of an enstatite crystal, an akermanite crystal, a diopside crystal, an anorthite crystal and a richerite crystal.

DETAILED DESCRIPTION OF THE INVENTION

The present invention will be described in detail hereunder. In the following description, glass-ceramics for attaining the first object of the invention are called "glass-ceramics $A_1$", a process of producing glass-ceramics for attaining the second object of the invention is called "process of producing glass-ceramics $A_2$", glass-ceramics for attaining the third object of the invention are called "glass-ceramics $B_1$", and a process of producing glass-ceramics for attaining the fourth object is called "process of producing glass-ceramics $B_2$".

The glass-ceramics $A_1$ will be now explained.

As described above, the glass-ceramics $A_1$ are produced by precipitating from glass containing CaO, $K_2O$, MgO, $SiO_2$, $Al_2O_3$ and a fluorine within a specific range, a calcium-potassium mica crystal and at least one crystal selected from the group consisting of an enstatite crystal, an akermanite crystal and a diopside crystal. The glass-ceramics $A_1$ have a desired hardness and are excellent in both mechanical strength and machinability. The reason of quantitative restriction with respect to the composition of the glass-ceramics $A_1$ is described below. When the CaO content is less than 2%, the amount of the mica crystal precipitated is reduced to deteriorate machinability. When the CaO content is more than 17%, the resulting glass has a high tendency of devitrification. Accordingly, the CaO content is restricted within a range of from 2 to 17%, preferably, within a range of from 5 to 15%. When the $K_2O$ content is less than 0.5%, the mica precipitated by heat treatment exhibits swellability. When the $K_2O$ content is more than 5%, the resulting glass has a high tendency of devitrification. Accordingly, the $K_2O$ content is restricted within a range of from 0.5 to 5%, preferably, within a range of from 1.0 to 3.5%. When the MgO content is less than 20%, the total amount of the precipitated crystals of silicates such as enstatite ($MgSiO_3$), akermanite ($2CaO.2Al_2O_3.5SiO_2$) and diopside ($CaO.MgO.2SiO_2$) is reduced to make it difficult to obtain glass-ceramics of high strength. When the MgO content is more than 35%, the amount of the precipitated mica is reduced undesirably. Accordingly, the MgO content is restricted within a range of from 20 to 35%, preferably, within a range of from 24 to 30%. When the $SiO_2$ content is less than 30%, not only the resulting glass has a high tendency of devitrification but the total amount of the precipitated crystals of silicates is reduced to make it very difficult to give high strength to glass-ceramics. When the $SiO_2$ content is more than 50%, the viscosity is increased to make it difficult to obtain homogeneous glass. Accordingly, the $SiO_2$ content is restricted within a range from 30 to 50%, preferably, within a range of from 40 to 49%. When the $Al_2O_3$ content is less than 5%, the resulting glass has a high tendency of devitrification. When the $Al_2O_3$ content is more than 30%, the viscosity is increased to make it difficult to obtain homogeneous glass. Accordingly, the $Al_2O_3$ content is restricted within a range of from 5 to 30%, preferably, within a range of from 7 to 17%. When the fluorine content (calculated as F) is less than 1.5%, precipitation of mica is so difficult that machinability cannot be given to glass-ceramics. When the fluorine content is more than 14%, the resulting glass is easily devitrified. Accordingly, the fluorine content is restricted within a range of from 1.5 to 14%, preferably, within a range of from 2 to 12%.

The glass-ceramics $A_1$ can contain, in addition to the above essential six components, at least one component selected from SrO, $TiO_2$, $Nb_2O_5$, $Ta_2O_5$, $Y_2O_3$ and $ZrO_2$ as a nucleating agent or a coloring agent in an amount of 5% or less. When the total content of these optional components is more than 5%, not only the resulting glass is easily devitrified to make it difficult to obtain homogeneous glass but the amount of the precipitated mica is reduced. Accordingly, it is preferable that the total content of the essential six components, that is, CaO, $K_2O$, MgO, $SiO_2$, $Al_2O_3$ and fluorine, is at least 95%.

The glass-ceramics $A_1$ can be produced by meting glass raw materials prepared to obtain a glass composition containing the following components of the following proportions,

|  | Percent by weight |
| --- | --- |
| CaO | 2 to 17 |
| $K_2O$ | 0.5 to 5 |
| MgO | 20 to 35 |
| $SiO_2$ | 30 to 50 |
| $Al_2O_3$ | 5 to 30 |
| Fluorine (calculated as F) | 1.5 to 14 | cooling the melt to room temperature to obtain transparent glass, and applying a step of heat treatment to the transparent glass in a temperature range in which a calcium-potassium mica crystal consisting of Ca—K—Mg—Al—Si—O—F and at least one crystal selected from the group consisting of an enstatite crystal, an akermanite crystal and a diopside crystal are precipitated.

The temperature range in which the respective crystals are precipitated can be obtained from the differential thermal analysis of the glass. By analyzing X-ray diffraction data of the glass heat-treated at each exothermic peak temperature in the differential thermal analysis curve, each precipitated crystal corresponding to the exothermic peak temperature is identified, so that each temperature range from the start of heat generation to its completion in the differential thermal analysis is taken as the temperature range in which each crystal is precipitated. Of the precipitated crystals, mica is necessary for improvement in machinability. Enstatite, akermanite and diopside are necessary for improvement in mechanical characteristics. The preferred temperature range in which the crystals are precipitated is 750° to 1200° C.

The glass-ceramics $A_1$ obtained by one step of heat treatment have a desired hardness and are excellent in mechanical strength and machinability. However, the glass-ceramics $A_1$ are not sufficient in light transmission property.

Therefore, the process of producing glass-ceramics $A_2$ is employed to obtain glass-ceramics having a desired hardness and being excellent in mechanical strength, machinability and light transmission property. The process of producing glass-ceramics $A_2$ comprises heating glass containing components being present within the ranges:

|  | Percent by weight |
| --- | --- |
| CaO | 2 to 17 |
| $K_2O$ | 0.5 to 5 |
| MgO | 20 to 35 |
| $SiO_2$ | 30 to 50 |
| $Al_2O_3$ | 5 to 30 |
| Fluorine (calculated as F) | 1.5 to 14 | at a temperature range higher than its glass transition point by a range of from 10° to 100° C. and then heating the glass at a temperature range higher than its glass transition point by a range of from 100° to 500° C., to thereby precipitate from the glass a calcium-potassium mica crystal consisting of Ca—K—Mg—Al—Si—O—F and at least one crystal selected from the group consisting of an enstatite crystal, an akermanite crystal and a diopside crystal. Not only the glass-ceramics $A_2$ thus produced have a desired hardness and are excellent in mechanical strength and machinability similarly to the glass-ceramics $A_1$ but also the glass-ceramics $A_2$ are more excellent in light transmission property than the glass-ceramics $A_1$.

In the two steps of heat treatment, the reason why the glass is heat-treated at a temperature range higher than its glass transition point by a range of from 10° to 100° C. in the first step of heat treatment is as follows. When the temperature in the first step of heat treatment is lower than a temperature which is higher than the glass transition point by 10° C., nuclei necessary for crystallization cannot be generated. When the temperature is higher than a temperature which is higher than the glass transition point by 100° C., not only growing of crystals but also generation of nuclei occurs to enlarge the particle size of the crystals so that light transmission property deteriorates. In short, the object of the first step of heat treatment is to generate securely nuclei in order to precipitate fine crystals.

It is preferable that the time required for the first step of heat treatment is 0.5 to 100 hours. The reason is as follows. When the time is shorter than 2 hours, nuclei cannot be generated sufficiently. When the time is more than 100 hours, the quantity of generated nuclei cannot be increased any more.

The reason why the glass having nuclei generated by the first step of heat treatment is heat-treated at a temperature range higher than its glass transition point by a range of from 100° to 500° C. in the second step of heat treatment is as follows. When the temperature in the second step of heat treatment is lower than a temperature which is higher than the glass transition point by 100° C., growing of crystals is insufficient. When the temperature is higher than a temperature which is higher than the glass transition point by 500° C., desired crystals of calcium-potassium mica and silicates such as enstatite and the like cannot be obtained. In short, the object of the second step of heat treatment is to grow respective crystals sufficiently.

It is preferable that the time required for the second step of heat treatment is 0.5 to 10 hours. The reason is as follows. When the time is shorter than 2 hours, growing of crystals is insufficient. When the time is more than 10 hours, the crystals cannot be grown any more.

In the process of producing glass-ceramics $A_2$, the glass transition point (Tg) of the glass is, in general, measured with a thermomechanical analyzer (TMA) according to Japan Optical Glass Industrial Standards JOGIS-1975 of the Japan Optical Glass Manufacturers' Association. Or it may be measured with a differential scanning calorimeter (DSC). Further, the glass transition point may be obtained by measuring specific heat.

In the following, glass-ceramics $B_1$ are described. As described above, the glass-ceramics $B_1$ are produced by precipitating from glass containing CaO, $K_2O$, $Na_2O$, MgO, $SiO_2$, $Al_2O_3$ and fluorine within a specific range, a calcium-potassium-sodium mica crystal and at least one crystal selected from the group consisting of an enstatite crystal, an akermanite crystal, a diopside crystal, an anorthite crystal and a richterite crystal. The glass-ceramics $B_1$ have a desired hardness and are excellent in mechanical strength, machinability and chemical durability. The reason of quantitative restriction with respect to the composition of the glass-ceramics $B_1$ is described below. The CaO content is restricted within a range of from 2 to 17%, preferably, within a range of from 5 to 15%, for the same reason as described above in the glass-ceramics $A_1$. The $K_2O$ content is restricted within a range of from 0.5 to 5%, preferably, within a range of from 1.0 to 3.5%, for the same reason as described above in the glass-ceramics $A_1$. $Na_2O$ not used in the glass-ceramics $A_1$ but used in the glass-ceramics $B_1$ has an effect of making the mica crystal fine to thereby reduce the amount of residual glass to thereby improve chemical durability. Corrosion resistance is related to the amount of residual glass. In short, chemical durability is improved as the amount of residual glass is reduced. However, when the $Na_2O$ content is less than 0.1%, the effect of making the mica crystal fine is small. When the $Na_2O$ content is more than 4.0%, a mica crystal containing a large amount of sodium is precipitated so that mechanical strength deteriorates undesirably. Accordingly, the $Na_2O$ content is restricted within a range of from 0.1 to 4%, preferably, within a range of from 0.5 to 1.8%. When the MgO content is less than 15%, the total amount of the precipitated crystals of silicates such as enstatite ($MgSiO_3$), akermanite ($2CaO.2Al_2O_3.5SiO_2$), diopside ($CaO.MgO.2SiO_2$) and anorthite ($CaO.Al_2O_3.2SiO_2$) is reduced to make it difficult to obtain glass-ceramics of high strength. When the MgO content is more than 35%, the amount of the precipitated mica is reduced undesirably. Accordingly, the MgO content is restricted within a range of from 15 to 35%, preferably, within a range of from 20 to 30%. When the $SiO_2$ content is less than 30%, not only the resulting glass has a high tendency of devitrification but the total amount of the precipitated crystals of silicates is reduced to make it very difficult to give high strength to glass-ceramics. When the $SiO_2$ content is more than 49%, the viscosity is increased to make it difficult to obtain homogeneous glass. Accordingly, the $SiO_2$ content is restricted within a range of from 30 to 49%, preferably, within a range of from 35 to 45%. The $Al_2O_3$ content is restricted within a range of from 5 to 30%, preferably, within a range of from 8 to 25%, for the same reason as described above in the glass-ceramics $A_1$. The fluorine content (calculated as F) is restricted within a range of from 1.5 to 14%, preferably, within a range of from 2 to 12%, for the same reason as described above in the glass-ceramics $A_1$.

The glass-ceramics $B_1$ can contain, in addition to the above essential seven components, at least one component selected from SrO, $TiO_2$, $Nb_2O_5$, $Ta_2O_5$, $Y_2O_3$ and $ZrO_2$ as a nucleating agent or a coloring agent. It is preferable that the total content of these optional components is 5% or less for the same reason as described above in the glass-ceramics $A_1$. Accordingly, it is preferable that the total content of the essential seven components, that is, $K_2O$, CaO, $Na_2O$, MgO, $SiO_2$, $Al_2O_3$ and fluorine, is at least 95%.

The glass-ceramics $B_1$ can be produced by meting glass raw materials prepared to obtain a glass composition containing the following components of the following proportions,

|  | Percent by weight |
| --- | --- |
| CaO | 2 to 17 |
| $K_2O$ | 0.5 to 5 |
| $Na_2O$ | 0.1 to 4 |
| MgO | 15 to 35 |
| $SiO_2$ | 30 to 49 |
| $Al_2O_3$ | 5 to 30 |
| Fluorine (calculated as F) | 1.5 to 14 | cooling the melt to room temperature to obtain transparent glass, and applying a step of heat treatment to the transparent glass in a temperature range in which a calcium-potassium mica crystal consisting of Ca—K—Na—Mg—Al—Si—O—F and at least one crystal selected from the group consisting of an enstatite crystal, an akermanite crystal, a diopside crystal, an anorthite crystal and a richterite crystal are precipitated.

The temperature range in which the respective crystals are precipitated can be obtained from X-ray diffraction data in the differential thermal analysis of the glass in the same manner as in the glass-ceramics $A_1$. Of the precipitated crystals, mica is necessary for improvement in machinability. Enstatite, akermanite, diopside, anorthite, richterite and the like are necessary for improvement in mechanical characteristics. The preferred temperature range in which the crystals are precipitated is 750° to 1200° C.

The glass-ceramics $B_1$ obtained by one step of heat treatment as described above have a desired hardness and are excellent in mechanical strength, machinability and chemical durability. However, the glass-ceramics $B_1$ are not sufficient in light transmission property.

Therefore, the process of producing glass-ceramics $B_2$ is employed to obtain glass-ceramics having a desired hardness and being excellent in mechanical strength, machinability, chemical durability and light transmission property. The process of producing glass-ceramics $B_2$ comprises heating glass containing components being present within the ranges:

|  | Percent by weight |
| --- | --- |
| CaO | 2 to 17 |
| $K_2O$ | 0.5 to 5 |
| $Na_2O$ | 0.1 to 4 |
| MgO | 15 to 35 |
| $SiO_2$ | 30 to 49 |
| $Al_2O_3$ | 5 to 30 |
| Fluorine (calculated as F) | 1.5 to 14 | at a temperature range higher than its glass transition point by a range of from 10° to 100° C. and then heating the glass at a temperature range higher than its glass transition point by a range of from 100° to 500° C., to thereby precipitate from the glass a calcium-potassium-sodium mica crystal consisting of Ca—K—Na—Mg—Al—Si—O—F and at least one crystal selected from the group consisting of an enstatite crystal, an akermanite crystal, a diopside crystal, an anorthite crystal and a richterite crystal. Not only the glass-ceramics $B_2$ thus produced have a desired hardness and are excellent in mechanical strength, machinability and chemical durability similarly to the glass-ceramics $B_1$ but also the glass-ceramics $B_2$ are more excellent in light transmission property than the glass-ceramics $B_1$.

In the two steps of heat treatment, the reason why the glass is heat-treated at a temperature range higher than its glass transition point by a range of from 10° to 100° C. in the first step of heat treatment is as described above in the process of producing glass-ceramics $A_2$.

It is preferable that the time required for the first step of heat treatment is 0.5 to 100 hours. The reason is as described above in the process of producing glass-ceramics $A_2$.

The reason why the glass having nuclei generated by the first step of heat treatment is heat-treated at a temperature range higher than its glass transition point by a range of from 100° to 500° C. in the second step of heat treatment is as described above in the process of producing glass-ceramics $A_2$.

It is preferable that the time required for the second step of heat treatment is 0.5 to 10 hours. The reason is as described above in the process of producing glass-ceramics $A_2$.

In the process of producing glass-ceramics $B_2$, the glass transition point (Tg) of the glass can be measured in the same manner as in the process of producing glass-ceramics $A_2$.

An artificial dental crown can be produced by using each of the glass-ceramics $A_1$, $A_2$, $B_1$ and $B_2$. In short, a dental crown made of each of the aforementioned glass-ceramics can be produced by lathing a block (for example, having a size of $20 \times 20 \times 50$ mm) of the glass-ceramics or by cutting it with a drill made of diamond, Carborundum, SiC, stainless steel or the like. Also, such a dental crown can be produced by a CAD/CAM system using a computer.

Further, such a dental crown of the glass-ceramics can be produced by mixing raw materials having a glass composition as defined above, heating the raw materials to prepare a glass melt, molding the glass melt into a desired dental crown shape, annealing it to room temperature to prepare bulk glass shaped like a dental crown, and applying heat treatment to the bulk glass.

The present invention will be described more in detail based on various examples, but the invention is not limited to the specific examples.

EXAMPLES 1 TO 21 (GLASS-CERAMICS $A_1$)

Glass raw materials as shown in Table 1 were prepared by using oxides, carbonates, fluorides and other materials, for example, $CaCO_3$, $K_2CO_3$, MgO, $MgF_2$, $Al_2O_3$, $SiO_2$ and the like. The glass raw materials were put into a platinum crucible and melted at a temperature of 1400° to 1550° C. for a period of 60 to 120 minutes. The melted glass was cast and then annealed to room temperature to prepare bulk glass. The bulk glass thus obtained was put into an electric furnace and heated from room temperature to a predetermined temperature within the range of from 800° to 1200° C. at a constant rate of 3° C./min, so that crystallization was made at the predetermined temperature for a period of 0.5 to 1 hour. Then, the resulting bulk glass in the furnace was cooled to room temperature, thus to produce glass-ceramics as Examples 1 to 21.

The respective glass-ceramics thus produced were pulverized, so that precipitated crystals were identified by X-ray diffraction. The respective glass-ceramics were examined for bending strength as mechanical strength by a three-point bending strength testing method (JIS R 1601). Further, the machinability of the respective glass-ceramics was judged by a 1.5 mm $\phi$ tool steel drill as classified into three groups: $\Delta$ as "Possible", $\bigcirc$ as "Good", and $\circledcirc$ as "Excellent". Further, the hardness of the respective glass-ceramics was measured with a Vickers hardness meter. Those results were collected into Table 1. As obvious from Table 1, the glass-ceramics in Examples 1 to 21 had a Vickers hardness of 320 to 450 kg/mm$^2$ as similar to the Vickers hardness of a natural tooth as about 370 kg/mm$^2$, had a high bending strength of 1700 to 3200 kg/cm$^2$, and were excellent in machinability.

TABLE 1 (1)

| | Example No. | | | |
|---|---|---|---|---|
| | 1 | 2 | 3 | 4 |
| CaO | 15 | 15 | 7.0 | 2.0 |
| $K_2O$ | 0.5 | 5 | 1.8 | 1.1 |
| MgO | 20.0 | 24.7 | 22.8 | 20.0 |
| $SiO_2$ | 50 | 38.5 | 46.3 | 42.9 |
| $Al_2O_3$ | 9.5 | 14.4 | 13.5 | 23.7 |
| F | 5.0 | 2.4 | 8.6 | 10.3 |
| Others | | | | |
| Heat treatment temp. (°C.) | 800 | 800 | 950 | 950 |
| Heat treatment time (hrs) | 10 | 10 | 2 | 2 |
| Precipitated crystal | Mica Akermanite | Mica Enstatite | Mica Diopside | Mica Diopside |
| Hardness | 420 | 450 | 340 | 370 |
| Bending strength | 1700 | 1700 | 2700 | 1700 |
| Machinability (result of cutting test) | $\bigcirc$ | $\Delta$ | $\circledcirc$ | $\circledcirc$ |

Hardness: measurement with a Vickers hardness meter (kg/mm$^2$)
Bending strength: measurement by a three-point bending strength testing method (JIS R 1601) (kg/cm$^2$)
Machinability (result of cutting test): estimation through cutting by a 1.5 mm $\phi$ tool steel drill ("Possible" —$\Delta$, "Good" —$\bigcirc$, and "Excellent" — $\circledcirc$ )

TABLE 1 (2)

| | Example No. | | | |
|---|---|---|---|---|
| | 5 | 6 | 7 | 8 |
| CaO | 8.8 | 7.9 | 4.9 | 4.5 |
| $K_2O$ | 1.6 | 3.4 | 1.6 | 3.2 |
| MgO | 26.1 | 30.0 | 21.3 | 22.4 |
| $SiO_2$ | 38.9 | 37.4 | 47.0 | 46.5 |
| $Al_2O_3$ | 15.7 | 12.5 | 15.7 | 19.2 |
| F | 8.9 | 8.8 | 9.5 | 4.2 |
| Others | | | | |
| Heat treatment temp. (°C.) | 950 | 1000 | 950 | 900 |
| Heat treatment time (hrs) | 2 | 0.5 | 1 | 3 |
| Precipitated crystal | Mica Diopside Enstatite | Mica Diopside Forsterite | Mica Diopside | Mica Enstatite Forsterite |
| Hardness | 320 | 400 | 420 | 370 |
| Bending strength | 3000 | 2000 | 1700 | 2100 |
| Machinability (result of cutting test) | $\circledcirc$ | $\circledcirc$ | $\circledcirc$ | $\circledcirc$ |

Hardness: measurement with a Vickers hardness meter (kg/mm$^2$)
Bending strength: measurement by a three-point bending strength testing method (JIS R 1601) (kg/cm$^2$)
Machinability (result of cutting test): estimation through cutting by a 1.5 mm $\phi$ tool steel drill ("Possible" —$\Delta$, "Good" —$\bigcirc$, and "Excellent" — $\circledcirc$ )

TABLE 1 (3)

| | Example No. | | | |
|---|---|---|---|---|
| | 9 | 10 | 11 | 12 |
| CaO | 16.6 | 10.6 | 7.0 | 3.2 |

TABLE 1 (3)-continued

| | Example No. | | | |
|---|---|---|---|---|
| | 9 | 10 | 11 | 12 |
| K₂O | 0.9 | 3.2 | 3.5 | 1.2 |
| MgO | 21.0 | 28.1 | 24.5 | 25.0 |
| SiO₂ | 30.0 | 30.0 | 48.0 | 39.2 |
| Al₂O₃ | 30.0 | 17.3 | 5.0 | 17.4 |
| F | 1.5 | 10.8 | 12.0 | 14.0 |
| Others | | | | |
| Heat treatment temp. (°C.) | 1200 | 950 | 1000 | 1000 |
| Heat treatment time (hrs) | 0.5 | 2 | 1 | 1 |
| Precipitated crystal | Mica Enstatite Akermanite | Mica Diopside | Mica Diopside | Mica Enstatite |
| Hardness | 340 | 360 | 380 | 320 |
| Bending strength | 2300 | 2700 | 2600 | 2400 |
| Machinability (result of cutting test) | ○ | ⊚ | ⊚ | ⊚ |

Hardness: measurement with a Vickers hardness meter (kg/mm²)
Bending strength: measurement by a three-point bending strength testing method (JIS R 1601) (kg/cm²)
Machinability (result of cutting test): estimation through cutting by a 1.5 mm φ tool steel drill ("Possible" —△, "Good" —○, and "Excellent" — ⊚ )

TABLE 1 (4)

| | Example No. | | | |
|---|---|---|---|---|
| | 13 | 14 | 15 | 16 |
| CaO | 3.2 | 5.2 | 10.1 | 6.1 |
| K₂O | 1.2 | 1.7 | 1.3 | 1.5 |
| MgO | 25.0 | 24.6 | 22.6 | 24.1 |
| SiO₂ | 39.2 | 42.4 | 44.1 | 44.3 |
| Al₂O₃ | 17.4 | 15.7 | 10.0 | 14.8 |
| F | 14.0 | 10.4 | 11.9 | 9.2 |
| Others | | | | |
| Heat treatment temp. (°C.) | 800 | 1000 | 950 | 950 |
| Heat treatment time (hrs) | 10 | 3 | 2 | 2 |
| Precipitated crystal | Mica Enstatite | Mica Diopside | Mica Akermanite | Mica Diopside |
| Hardness | 410 | 330 | 410 | 400 |
| Bending strength | 2400 | 3200 | 2000 | 2300 |
| Machinability (result of cutting test) | ⊚ | ⊚ | ⊚ | ⊚ |

Hardness: measurement with a Vickers hardness meter (kg/mm²)
Bending strength: measurement by a three-point bending strength testing method (JIS R 1601) (kg/cm²)
Machinability (result of cutting test): estimation through cutting by a 1.5 mm φ tool steel drill ("Possible" —△, "Good" —○, and "Excellent" — ⊚ )

TABLE 1 (5)

| | Example No. | | | |
|---|---|---|---|---|
| | 17 | 18 | 19 | 20 |
| CaO | 6.3 | 4.3 | 6.5 | 6.0 |
| K₂O | 2.1 | 1.7 | 1.7 | 1.5 |
| MgO | 28.2 | 35.0 | 25.5 | 24.1 |
| SiO₂ | 43.4 | 33.0 | 43.5 | 43.5 |
| Al₂O₃ | 11.4 | 16.0 | 12.7 | 12.7 |
| F | 8.6 | 10.0 | 10.1 | 9.2 |
| Others | | | | SrO 1.5 TiO₂ 0.5 Y₂O₃ 1.0 |
| Heat treatment temp. (°C.) | 950 | 950 | 950 | 950 |
| Heat treatment time (hrs) | 2 | 2 | 2 | 2 |
| Precipitated crystal | Mica Enstatite | Mica Diopside | Mica Diopside | Mica Diopside |
| Hardness | 400 | 350 | 340 | 350 |
| Bending strength | 2500 | 3000 | 3000 | 2700 |
| Machinability (result of cutting test) | ⊚ | ⊚ | ⊚ | ⊚ |

Hardness: measurement with a Vickers hardness meter (kg/mm²)
Bending strength: measurement by a three-point bending strength testing method (JIS R 1601) (kg/cm²)
Machinability (result of cutting test): estimation through cutting by a 1.5 mm φ tool steel drill ("Possible" —△, "Good" —○, and "Excellent" — ⊚ )

TABLE 1 (6)

| | Example No. 21 |
|---|---|
| CaO | 6.0 |
| K₂O | 1.5 |
| MgO | 22.1 |
| SiO₂ | 43.5 |
| Al₂O₃ | 12.7 |
| F | 9.2 |
| Others | Nb₂O₅ 0.5 Ta₂O₅ 1.5 ZrO₂ 3.0 |
| Heat treatment temp. (°C.) | 950 |
| Heat treatment time (hrs) | 2 |
| Precipitated crystal | Mica Diopside |
| Hardness | 370 |
| Bending strength | 2400 |
| Machinability (result of cutting test) | ⊚ |

Hardness: measurement with a Vickers hardness meter (kg/mm²)
Bending strength: measurement by a three-point bending strength testing method (JIS R 1601) (kg/cm²)
Machinability (result of cutting test): estimation through cutting by a 1.5 mm φ tool steel drill ("Possible" —△, "Good" —○, and "Excellent" — ⊚ )

EXAMPLES 22 TO 28 (PROCESS OF PRODUCING GLASS-CERAMICS A₂)

Glass raw materials as shown in Table 2 were prepared by using oxides, carbonates, fluorides and other materials, for example, CaCO₃, K₂CO₃, MgO, MgF₂, Al₂O₃, SiO₂ and the like. The glass raw materials were put into a platinum crucible and melted at a temperature of 1400° to 1550° C. for a period of 60 to 120 minutes. The melted glass was cast and then annealed to room temperature to prepare bulk glass. The bulk glass thus obtained was put into an electric furnace, heated from room temperature to a predetermined temperature within the range of from 550° to 800° C. (corresponding to temperatures higher than its glass transition point by the range of from 10° to 100° C.) at a constant rate of 3° C./min, and kept at the predetermined temperature for a period of 0.5 to 100 hours. Then, the bulk glass was heated to a predetermined temperature within the range of from 800° to 1200° C. (corresponding to temperatures higher than its glass transition point by the range of from 100° to 500° C.) at a constant rate of 3° C./min, so that crystallization was made at the predetermined temperature for a period of 2 to 10 hours. The resulting bulk glass in the furnace was cooled to room temperature, thus to produce glass-ceramics as Examples 22 to 28.

The respective glass-ceramics thus produced were pulverized, so that precipitated crystals were identified by X-ray diffraction. The respective glass-ceramics were examined for Vickers hardness, bending strength and machinability in the same manner as in Examples 1 to 21. Those results were collected into Table 2. As obvious from Table 2, the glass-ceramics in Examples 22 to 28 had a Vickers hardness of 340 to 450 kg/mm$^2$ as similar to the Vickers hardness of a natural tooth, had a high bending strength of 1700 to 3000 kg/cm$^2$, and were excellent in machinability. Further, the respective glass-ceramics were examined for light transmission property by eye estimation. As a result, the glass-ceramics in Examples 22 to 28 had excellent light transmission property (represented by the estimation symbol ⊚ in Table 2).

TABLE 2 (1)

|  |  | Example No. | | | |
|---|---|---|---|---|---|
|  |  | 22 | 23 | 24 | 25 |
|  | CaO | 10.1 | 6.1 | 6.3 | 4.3 |
|  | K$_2$O | 1.3 | 1.5 | 2.1 | 1.7 |
|  | MgO | 22.6 | 24.1 | 28.2 | 35.0 |
|  | SiO$_2$ | 44.1 | 44.3 | 43.4 | 33.0 |
|  | Al$_2$O$_3$ | 10.0 | 14.8 | 11.4 | 16.0 |
|  | F | 11.9 | 9.2 | 8.6 | 10.0 |
|  | Others |  |  |  |  |
| 1st | temp. (°C.) | 650 | 650 | 700 | 720 |
|  | time (hrs) | 10 | 5 | 5 | 10 |
| 2nd | temp. (°C.) | 950 | 970 | 950 | 980 |
|  | time (hrs) | 2 | 2 | 2 | 2 |
| Precipitated crystal |  | Mica Akermanite | Mica Diopside | Mica Enstatite | Mica Diopside |
| Hardness |  | 420 | 410 | 390 | 340 |
| Bending strength |  | 2000 | 2300 | 2500 | 3000 |
| Machinability (result of cutting test) |  | ⊚ | ⊚ | ⊚ | ⊚ |
| Light transmission |  | ⊚ | ⊚ | ⊚ | ⊚ |

Hardness: measurement with a Vickers hardness meter (kg/mm$^2$)
Bending strength: measurement by a three-point bending strength testing method (JIS R 1601) (kg/cm$^2$)
Machinability (result of cutting test): estimation through cutting by a 1.5 mm φ tool steel drill ("Possible" —Δ, "Good" —◯, and "Excellent" —⊚)
Light transmission: eye estimation ("Excellent" —⊚, and "Good" —◯)

TABLE 2 (2)

|  |  | Example No. | | |
|---|---|---|---|---|
|  |  | 26 | 27 | 28 |
|  | CaO | 6.5 | 2.0 | 6.0 |
|  | K$_2$O | 1.7 | 1.1 | 1.5 |
|  | MgO | 25.5 | 20.0 | 24.1 |
|  | SiO$_2$ | 43.5 | 42.9 | 43.5 |
|  | Al$_2$O$_3$ | 12.7 | 23.7 | 15.7 |
|  | F | 10.1 | 10.3 | 9.2 |
|  | Others |  |  |  |
| 1st | temp. (°C.) | 670 | 600 | 650 |
|  | time (hrs) | 20 | 100 | 30 |
| 2nd | temp. (°C.) | 940 | 950 | 900 |
|  | time (hrs) | 2 | 2 | 2 |
| Precipitated crystal |  | Mica Diopside | Mica Enstatite Diopside | Mica Enstatite Diopside |
| Hardness |  | 340 | 450 | 400 |
| Bending strength |  | 3000 | 1700 | 2400 |
| Machinability (result of cutting test) |  | ⊚ | ⊚ | ⊚ |
| Light transmission |  | ⊚ | ⊚ | ⊚ |

Hardness: measurement with a Vickers hardness meter (kg/mm$^2$)
Bending strength: measurement by a three-point bending strength testing method (JIS R 1601) (kg/cm$^2$)
Machinability (result of cutting test): estimation through cutting by a 1.5 mm φ tool steel drill ("Possible" —Δ, "Good" —◯, and "Excellent" —⊚ )
Light transmission: eye estimation ("Excellent" —⊚, and "Good" —◯)

EXAMPLES 29 TO 49 (GLASS-CERAMICS B$_1$)

Glass raw materials as shown in Table 3 were prepared by using oxides, carbonates, fluorides and other materials, for example, CaCO$_3$, K$_2$CO$_3$, Na$_2$CO$_3$, MgO, MgF$_2$, Al$_2$O$_3$, SiO$_2$ and the like. The glass raw materials were put into a platinum crucible and melted at a temperature of 1400° to 1550° C. for a period of 60 to 120 minutes. The melted glass was cast and then annealed to room temperature to prepare bulk glass. The bulk glass thus obtained was put into an electric furnace and heated from room temperature to a predetermined temperature within the range of from 800° to 1200° C. at a constant rate of 3° C./min, so that crystallization was made at the predetermined temperature for a period of 0.5 to 10 hours. The resulting bulk glass in the furnace was cooled to room temperature, thus to produce glass-ceramics as Examples 29 to 49.

The respective glass-ceramics thus produced were pulverized in the same manner as in Examples 1 to 21, so that precipitated crystals were identified by X-ray diffraction. The respective glass-ceramics were examined for bending strength and machinability in the same manner as in Examples 1 to 21. Further, the chemical durability of the glass-ceramics was estimated as follows. After the glass-ceramics were soaked respectively in 90 ml of an aqueous solution of 10% HCl and in 90 ml of an aqueous solution of 10% NaOH at room temperature for 24 hours, reduction of the weight was measured as data exhibiting acid resistance and alkali resistance. Those results were collected into Table 3. As obvious from Table 3, the glass-ceramics in Examples 29 to 49 had a Vickers hardness of 320 to 480 kg/mm$^2$ as similar to the Vickers hardness of about 370 kg/mm$^2$ in an enamel portion of a natural tooth, had a high bending strength of 2000 to 3200 kg/cm$^2$, and were passable in machinability. In addition, the respective glass-ceramics were so excellent in chemical durability that the acid resistance and the alkali resistance thereof exhibited the range of from 0.20 to 0.50 mg/cm$^2$ and the range of from 0.011 to 0.049 mg/cm$^2$, respectively.

TABLE 3 (1)

|  | Example No. | | | |
|---|---|---|---|---|
|  | 29 | 30 | 31 | 32 |
| CaO | 7.5 | 16.5 | 3.4 | 2.3 |
| K$_2$O | 3.3 | 4.8 | 1.4 | 0.7 |
| Na$_2$O | 3.5 | 0.2 | 1.0 | 2.3 |
| MgO | 34.7 | 22.5 | 17.2 | 20.3 |
| SiO$_2$ | 30.7 | 45.0 | 49.0 | 43.5 |
| Al$_2$O$_3$ | 12.3 | 5.3 | 24.6 | 22.9 |
| F | 8.0 | 5.7 | 3.4 | 8.0 |
| Others |  |  |  |  |
| Heat treatment temp. (°C.) | 800 | 800 | 950 | 950 |
| Heat treatment time (hrs) | 10 | 10 | 2 | 2 |
| Precipitated crystal | Mica Enstatite | Mica Enstatite | Mica Anorthite | Mica Anorthite |
| Hardness | 370 | 380 | 320 | 360 |
| Bend strength | 2000 | 2500 | 2700 | 3000 |
| Machinability (result of cutting test) | ◯ | ◯ | ⊚ | ◯ |
| Acid durability | 0.50 | 0.45 | 0.30 | 0.23 |
| Alkali durability | 0.038 | 0.029 | 0.021 | 0.012 |

Hardness: measurement with a Vickers hardness meter (kg/mm$^2$)
Bending strength: measurement by a three-point bending strength testing method (JIS R 1601) (kg/cm$^2$)
Machinability (result of cutting test): estimation through cutting by a 1.5 mm φ tool steel drill ("Possible" —Δ, "Good" —◯, and "Excellent" —⊚)
Acid durability, alkali durability: measurement of weight loss after soaked respectively in 90 ml of an aqueous solution of 10% HCl and in 90 ml of an aqueous solution of 10% NaOH for 24 hours in room temperature (mg/cm$^2$)

TABLE 3 (2)

| | Example No. | | | |
|---|---|---|---|---|
| | 33 | 34 | 35 | 36 |
| CaO | 6.0 | 5.9 | 6.5 | 9.8 |
| $K_2O$ | 2.5 | 2.5 | 2.7 | 4.1 |
| $Na_2O$ | 0.9 | 1.9 | 0.9 | 3.9 |
| MgO | 24.5 | 24.3 | 26.0 | 16.0 |
| $SiO_2$ | 45.1 | 44.7 | 44.3 | 49.6 |
| $Al_2O_3$ | 13.1 | 13.0 | 10.8 | 9.6 |
| F | 7.9 | 7.7 | 8.8 | 7.0 |
| Others | | | | |
| Heat treatment temp. (°C.) | 950 | 1000 | 950 | 900 |
| Heat treatment time (hrs) | 2 | 0.5 | 1 | 3 |
| Precipitated crystal | Mica Anorthite Enstatite | Mica Richterite Forsterite Enstatite | Mica Diopside Richterite Enstatite | Mica Richterite Diopside |
| Hardness | 410 | 450 | 430 | 320 |
| Bend strength | 2600 | 2200 | 2700 | 2000 |
| Machinability (result of cutting test) | ○ | △ | ○ | ○ |
| Acid durability | 0.30 | 0.24 | 0.29 | 0.24 |
| Alkali durability | 0.011 | 0.013 | 0.036 | 0.019 |

Hardness: measurement with a Vickers hardness meter ($kg/mm^2$)
Bending strength: measurement by a three-point bending strength testing method (JIS R 1601) ($kg/cm^2$)
Machinability (result of cutting test): estimation through cutting by a 1.5 mm φ tool steel drill ("Possible" —△, "Good" —○, and "Excellent" —◎)
Acid durability, alkali durability: measurement of weight loss after soaked respectively in 90 ml of an aqueous solution of 10% HCl and in 90 ml of an aqueous solution of 10% NaOH for 24 hours in room temperature ($mg/cm^2$)

TABLE 3 (3)

| | Example No. | | | |
|---|---|---|---|---|
| | 37 | 38 | 39 | 40 |
| CaO | 8.3 | 10.6 | 7.5 | 2.6 |
| $K_2O$ | 0.9 | 2.7 | 2.8 | 0.8 |
| $Na_2O$ | 3.8 | 0.5 | 1.9 | 0.9 |
| MgO | 21.0 | 28.1 | 20.1 | 22.5 |
| $SiO_2$ | 34.5 | 30.0 | 47.0 | 43.5 |
| $Al_2O_3$ | 30.0 | 17.3 | 14.1 | 15.7 |
| F | 1.5 | 10.8 | 6.6 | 14.0 |
| Others | | | | |
| Heat treatment temp. (°C.) | 1200 | 950 | 1000 | 1000 |
| Heat treatment time (hrs) | 0.5 | 2 | 1 | 1 |
| Precipitated crystal | Mica Richterite Forsterite | Mica Diopside | Mica Richterite Diopside | Mica Enstatite |
| Hardness | 480 | 400 | 410 | 350 |
| Bend strength | 2500 | 2700 | 3000 | 2600 |
| Machinability (result of cutting test) | △ | ○ | ◎ | ○ |
| Acid durability | 0.20 | 0.27 | 0.32 | 0.39 |
| Alkali durability | 0.015 | 0.016 | 0.013 | 0.027 |

Hardness: measurement with a Vickers hardness meter ($kg/mm^2$)
Bending strength: measurement by a three-point bending strength testing method (JIS R 1601) ($kg/cm^2$)
Machinability (result of cutting test): estimation through cutting by a 1.5 mm φ tool steel drill ("Possible" —△, "Good" —○, and "Excellent" —◎)
Acid durability, alkali durability: measurement of weight loss after soaked respectively in 90 ml of an aqueous solution of 10% HCl and in 90 ml of an aqueous solution of 10% NaOH for 24 hours in room temperature ($mg/cm^2$)

TABLE 3 (4)

| | Example No. | | | |
|---|---|---|---|---|
| | 41 | 42 | 43 | 44 |
| CaO | 3.2 | 8.0 | 6.1 | 5.2 |
| $K_2O$ | 1.0 | 3.0 | 1.7 | 2.0 |
| $Na_2O$ | 0.2 | 1.9 | 2.5 | 0.9 |
| MgO | 25.0 | 21.6 | 22.6 | 20.3 |
| $SiO_2$ | 39.2 | 46.1 | 48.7 | 45.2 |
| $Al_2O_3$ | 17.4 | 11.9 | 6.5 | 17.0 |
| F | 14.0 | 7.5 | 11.9 | 8.9 |
| Others | | | | |
| Heat treatment temp. (°C.) | 800 | 1000 | 950 | 950 |
| Heat treatment time (hrs) | 10 | 3 | 2 | 2 |
| Precipitated crystal | Mica Enstatite | Mica Diopside Richterite | Mica Akermanite Richterite | Mica Enstatite |
| Hardness | 410 | 450 | 320 | 330 |
| Bend strength | 2200 | 2700 | 2600 | 2400 |
| Machinability (result of cutting test) | ○ | ○ | ◎ | ◎ |
| Acid durability | 0.37 | 0.32 | 0.33 | 0.32 |
| Alkali durability | 0.026 | 0.021 | 0.042 | 0.049 |

Hardness: measurement with a Vickers hardness meter ($kg/mm^2$)
Bending strength: measurement by a three-point bending strength testing method (JIS R 1601) ($kg/cm^2$)
Machinability (result of cutting test): estimation through cutting by a 1.5 mm φ tool steel drill ("Possible" —△, "Good" —○, and "Excellent" —◎)
Acid durability, alkali durability: measurement of weight loss after soaked respectively in 90 ml of an aqueous solution of 10% HCl and in 90 ml of an aqueous solution of 10% NaOH for 24 hours in room temperature ($mg/cm^2$)

TABLE 3 (5)

| | Example No. | | | |
|---|---|---|---|---|
| | 45 | 46 | 47 | 48 |
| CaO | 6.3 | 4.9 | 4.3 | 6.0 |
| $K_2O$ | 2.1 | 1.8 | 1.5 | 2.5 |
| $Na_2O$ | 0.5 | 1.0 | 1.0 | 0.9 |
| MgO | 27.7 | 20.0 | 34.6 | 21.5 |
| $SiO_2$ | 43.4 | 47.4 | 33.0 | 45.1 |
| $Al_2O_3$ | 11.4 | 19.7 | 17.8 | 13.1 |
| F | 8.6 | 5.2 | 7.8 | 7.9 |
| Others | | | | SrO 1.5 $TiO_2$ 0.5 $Y_2O_3$ 1.0 |
| Heat treatment temp. (°C.) | 950 | 950 | 950 | 950 |
| Heat treatment time (hrs) | 2 | 2 | 2 | 2 |
| Precipitated crystal | Mica Enstatite | Mica Enstatite | Mica Diopside | Mica Diopside |
| Hardness | 410 | 340 | 380 | 320 |
| Bend strength | 3000 | 2700 | 2600 | 2300 |
| Machinability (result of cutting test) | ○ | ◎ | ○ | ○ |
| Acid durability | 0.26 | 0.27 | 0.45 | 0.25 |
| Alkali durability | 0.032 | 0.029 | 0.045 | 0.031 |

Hardness: measurement with a Vickers hardness meter ($kg/mm^2$)
Bending strength: measurement by a three-point bending strength testing method (JIS R 1601) ($kg/cm^2$)
Machinability (result of cutting test): estimation through cutting by a 1.5 mm φ tool steel drill ("Possible" —△, "Good" —○, and "Excellent" —◎)
Acid durability, alkali durability: measurement of weight loss after soaked respectively in 90 ml of an aqueous solution of 10% HCl and in 90 ml of an aqueous solution of 10% NaOH for 24 hours in room temperature ($mg/cm^2$)

TABLE 3 (6)

| | Example No. 49 |
|---|---|
| CaO | 6.0 |
| $K_2O$ | 2.5 |
| $Na_2O$ | 0.9 |
| MgO | 20.5 |
| $SiO_2$ | 45.1 |
| $Al_2O_3$ | 12.1 |
| F | 7.9 |
| Others | $Nb_2O_5$ 0.5 $Ta_2O_5$ 1.5 $ZrO_2$ 3.0 |
| Heat treatment temp. (°C.) | 950 |
| Heat treatment | 2 |

TABLE 3 (6)-continued

| | Example No. |
| --- | --- |
| | 49 |
| time (hrs) | |
| Precipitated | Mica |
| crystal | Diopside |
| Hardness | 320 |
| Bend strength | 3200 |
| Machinability (result of cutting test) | ○ |
| Acid durability | 0.29 |
| Alkali durability | 0.036 |

Hardness: measurement with a Vickers hardness meter (kg/mm²)
Bending strength: measurement by a three-point bending strength testing method (JIS R 1601) (kg/cm²)
Machinability (result of cutting test): estimation through cutting by a 1.5 mm φ tool steel drill ("Possible" —Δ, "Good" —○, and "Excellent" —⊙)
Acid durability, alkali durability: measurement of weight loss after soaked respectively in 90 ml of an aqueous solution of 10% HCl and in 90 ml of an aqueous solution of 10% NaOH for 24 hours in room temperature (mg/cm²)

EXAMPLES 50 TO 56 (PROCESS OF PRODUCING GLASS-CERAMICS B₂)

Glass raw materials as shown in Table 4 were prepared by using oxides, carbonates, fluorides and other materials, for example, $CaCO_3$, $K_2CO_3$, $Na_2CO_3$, $MgO$, $MgF_2$, $Al_2O_3$, $SiO_2$ and the like. The glass raw materials were put into a platinum crucible and melted at a temperature of 1400° to 1550° C. for a period of 60 to 120 minutes. The melted glass was cast and then annealed to room temperature to prepare bulk glass. The bulk glass thus obtained was put into an electric furnace, heated from room temperature to a predetermined temperature within the range of from 550° to 800° C. (corresponding to temperatures higher than its glass transition point by the range of from 10° to 100° C.) at a constant rate of 3° C./min, and kept at the predetermined temperature for a period of 0.5 to 100 hours. Then, the bulk glass was heated to a predetermined temperature within the range of from 800° to 1200° C. (corresponding to temperatures higher than its glass transition point by the range of from 100° to 500° C.) at a constant rate of 3° C./min, so that crystallization was made at the predetermined temperature for a period of 0.5 to 10 hours. The resulting bulk glass in the furnace was cooled to room temperature, thus to produce glass-ceramics as Examples 50 to 56.

The respective glass-ceramics thus produced were pulverized, so that precipitated crystals were identified by X-ray diffraction. The respective glass-ceramics were examined for Vickers hardness, bending strength, machinability and chemical durability in the same manner as in Examples 39 to 49. Further, the respective glass-ceramics were examined for light transmission property by eye estimation. Those results were collected into Table 4. As obvious from Table 4, the glass-ceramics in Examples 50 to 56 had a Vickers hardness of 320 to 410 kg/mm² as similar to the Vickers hardness of a natural tooth, had a high bending strength of 2400 to 3300 kg/cm², and were passable in machinability. Further, the respective glass-ceramics were excellent in light transmission property. In addition, the respective glass-ceramics were so excellent in chemical durability that the acid resistance and the alkali resistance thereof exhibited the range of from 0.20 to 0.45 mg/cm² and the range of from 0.021 to 0.053 mg/cm², respectively.

TABLE 4 (1)

| | | Example No. | | | |
| --- | --- | --- | --- | --- | --- |
| | | 50 | 51 | 52 | 53 |
| CaO | | 5.2 | 4.9 | 6.3 | 4.3 |
| K₂O | | 2.0 | 1.8 | 2.1 | 1.7 |
| Na₂O | | 0.9 | 1.0 | 2.7 | 1.5 |
| MgO | | 20.8 | 20.0 | 25.5 | 35.0 |
| SiO₂ | | 45.2 | 47.4 | 43.4 | 41.0 |
| Al₂O₃ | | 17.0 | 19.7 | 11.4 | 10.0 |
| F | | 8.9 | 5.2 | 8.6 | 6.5 |
| Others | | | | | |
| 1st | temp. (°C.) | 650 | 650 | 700 | 720 |
| | time (hrs) | 10 | 5 | 5 | 10 |
| 2nd | temp. (°C.) | 950 | 970 | 950 | 980 |
| | time (hrs) | 2 | 2 | 2 | 2 |
| Precipitated | | Mica | Mica | Mica | Mica |
| crystal | | Enstatite | Enstatite | Enstatite | Diopside |
| Hardness | | 320 | 330 | 410 | 340 |
| Bend strength | | 2600 | 2700 | 3000 | 2700 |
| Machinability (result of cutting test) | | ○ | ○ | ○ | ⊙ |
| Transmission | | ○ | ○ | ○ | ○ |
| Acid durability | | 0.29 | 0.23 | 0.45 | 0.38 |
| Alkali durability | | 0.021 | 0.029 | 0.036 | 0.030 |

Hardness: measurement with a Vickers hardness meter (kg/mm²)
Bending strength: measurement by a three-point bending strength testing method (JIS R 1601) (kg/cm²)
Machinability (result of cutting test): estimation through cutting by a 1.5 mm φ tool steel drill ("Possible" —Δ, "Good" —○, and "Excellent" —⊙)
Light transmission: eye estimation ("Excellent" —⊙, and "Good" —○)
Acid durability, alkali durability: measurement of weight loss after soaked respectively in 90 ml of an aqueous solution of 10% HCl and in 90 ml of an aqueous solution of 10% NaOH for 24 hours in room temperature (mg/cm²)

TABLE 4 (2)

| | | Example No. | | |
| --- | --- | --- | --- | --- |
| | | 54 | 55 | 56 |
| CaO | | 6.5 | 2.0 | 7.5 |
| K₂O | | 1.7 | 1.1 | 1.5 |
| Na₂O | | 2.0 | 0.8 | 2.8 |
| MgO | | 23.5 | 15.1 | 23.8 |
| SiO₂ | | 43.5 | 47.9 | 43.5 |
| Al₂O₃ | | 12.7 | 23.2 | 12.4 |
| F | | 10.1 | 9.9 | 8.8 |
| Others | | | | |
| 1st | temp. (°C.) | 670 | 600 | 650 |
| | time (hrs) | 20 | 100 | 30 |
| 2nd | temp. (°C.) | 940 | 950 | 900 |
| | time (hrs) | 2 | 2 | 2 |
| Precipitated | | Mica | Mica | Mica |
| crystal | | Diopside | Enstatite | Enstatite |
| | | Richterite | Diopside | Diopside |
| Hardness | | 380 | 320 | 320 |
| Bend strength | | 2400 | 2400 | 3300 |
| Machinability (result of cutting test) | | ○ | ○ | Δ |
| Transmission | | ○ | ○ | ○ |
| Acid durability | | 0.41 | 0.20 | 0.42 |
| Alkali durability | | 0.053 | 0.042 | 0.038 |

Hardness: measurement with a Vickers hardness meter (kg/mm²)
Bending strength: measurement by a three-point bending strength testing method (JIS R 1601) (kg/cm²)
Machinability (result of cutting test): estimation through cutting by a 1.5 mm φ tool steel drill ("Possible" —Δ, "Good" —○, and "Excellent" —⊙)
Light transmission: eye estimation ("Excellent" —⊙, and "Good" —○)
Acid durability, alkali durability: measurement of weight loss after soaked respectively in 90 ml of an aqueous solution of 10% HCl and in 90 ml of an aqueous solution

EXAMPLE 57 (ARTIFICIAL DENTAL CROWN)

A glass composition in Example 5 was melted at 1500° C. for 90 minutes. The melted glass was cast in a mold made of a dental non-gypsum refractory casting investments and then annealed to room temperature to prepare bulk glass shaped like a dental crown. The bulk glass thus obtained was put into an electric furnace and heated from room temperature to 950° C. at a constant rate of 3° C./min, so that crystallization was made at the predetermined temperature for 2 hours. Then, the resulting bulk glass in the furnace was cooled to room temperature, thus to produce a desired-form artificial dental crown made of glass-ceramics.

EXAMPLE 58 (ARTIFICIAL CROWN OF TOOTH)

Bulk glass shaped like a dental crown was prepared by using a glass composition defined in Example 26 in the same manner as in Example 57.

The bulk glass thus obtained was put into an electric furnace, heated from room temperature to 670° C. at a constant rate of 3° C./min, and kept at the temperature for 20 hours. Then, the resulting bulk glass was further heated to 940° C. at a constant rate of 3° C./min, so that crystallization was made at the temperature for 2 hours. Then, the resulting bulk glass in the furnace was cooled to room temperature, thus to produce an artificial dental crown of glass-ceramics having a predetermined shape and having light transmission property.

EXAMPLE 59 (ARTIFICIAL CROWN OF TOOTH)

A 20×20×50 mm block was cut down out of glass-ceramics obtained in Example 33. The block was treated by use of a lathe and a drilling machine, thus to produce a desired-form artificial crown made of glass-ceramics.

EXAMPLE 60 (ARTIFICIAL DENTAL CROWN)

An artificial crown of glass-ceramics having light transmission property was produced from glass-ceramics having light transmission property, obtained in Example 55, in the same manner as in Example 59.

As described above, glass-ceramics $A_1$ produced by precipitating from glass containing CaO, $K_2O$, MgO, $SiO_2$, $Al_2O_3$ and fluorine within a specific range, a calcium-potassium mica crystal and at least one crystal selected from the group consisting of an enstatite crystal, an akermanite crystal and a diopside crystal have an advantage in that the glass-ceramics have a desired hardness and are excellent in both mechanical strength and machinability. Further, glass-ceramics $A_2$ having a desired hardness and being excellent in mechanical strength, machinability and light transmission property can be produced by applying two steps of heat treatment to the aforementioned glass.

On the other hand, glass-ceramics $B_1$ produced by precipitating from glass containing CaO, $K_2O$, $Na_2O$, MgO, $SiO_2$, $Al_2O_3$ and fluorine within a specific range, a calcium-potassium-sodium mica crystal and at least one crystal selected from the group consisting of an enstatite crystal, an akermanite crystal, a diopside crystal, an anorthite crystal and a richterite crystal have an advantage in that the glass-ceramics have a desired hardness and are excellent in mechanical strength, machinability and chemical durability. Further, glass-ceramics $B_2$ having a desired hardness and being excellent in mechanical strength, machinability, chemical durability and light transmission property can be produced by applying two steps of heat treatment to the aforementioned glass.

In addition, an excellent artificial dental crown can be produced from these kinds of glass-ceramics.

What is claimed is:

1. A glass ceramics produced by precipitating from glass a calcium-potassium mica crystal consisting of Ca—K—Mg—Al—Si—O—F and at least one crystal selected from the group consisting of an enstatite crystal, an akermanite crystal and a diopside crystal, said glass containing components being present within the ranges as follows:

|  | Percent of weight |
|---|---|
| CaO | 2 to 17 |
| $K_2O$ | 0.5 to 5 |
| MgO | 20 to 35 |
| $SiO_2$ | 30 to 50 |
| $Al_2O_3$ | 5 to 30 |
| Fluorine (calculated as F) | 1.5 to 14. |

2. A glass-ceramics according to claim 1, wherein said glass contains at least one component selected from the group consisting of SrO, $TiO_2$, $Nb_2O_5$, $Ta_2O_5$, $Y_2O_3$ and $ZrO_2$ in an amount of 5% or less.

3. Glass-ceramics produced by precipitating from glass a calcium-potassium-sodium mica crystal consisting of Ca—K—Na—Mg—Al—Si—O—F and at least one crystal selected from the group consisting of an enstatite crystal, an akermanite crystal, a diopside crystal, an anorthite crystal and a richterite crystal, said glass containing components being present within the ranges as follows:

|  | Percent by weight |
|---|---|
| CaO | 2 to 17 |
| $K_2O$ | 0.5 to 5 |
| $Na_2O$ | 0.1 to 4 |
| MgO | 15 to 35 |
| $SiO_2$ | 30 to 49 |
| $Al_2O_3$ | 5 to 30 |
| Fluorine (calculated as F) | 1.5 to 14. |

4. The glass-ceramics according to claim 3, wherein said glass contains at least one component selected from the group consisting of SrO, $TiO_2$, $Nb_2O_5$, $Ta_2O_5$, $Y_2O_3$ and $ZrO_2$ in an amount of 5% of less.

5. An artificial dental crown comprising the glass-ceramics of any one of claims 1, 2, 3 or 4.

6. An artificial dental crown comprising a glass-ceramics produced by the process of heating glass-containing components, present within the ranges as follows:

|  | Percent by weight |
|---|---|
| CaO | 2 to 17 |
| $K_2O$ | 0.5 to 5 |
| MgO | 20 to 35 |
| $SiO_2$ | 30 to 50 |
| $Al_2O_3$ | 5 to 30 |
| Fluorine (calculated as F) | 1.5 to 14 | successively at a temperature higher than the glass transition point by a range of from 10° to 100° C. and at a temperature higher than its glass transition point by a range of from 100° to 500° C., to thereby precipitate from the glass a calcium-potassium mica crystal consisting of Ca—K—Mg—Al—Si—O—F and at least one crystal selected from the group consisting of an enstatite crystal, an akermanite crystal and a diopside crystal.

7. The artificial dental crown of claim 6, wherein said glass contains at least one component selected from the group consisting of SrO, TiO$_2$, Nb$_2$O$_5$, Ta$_2$O$_5$, Y$_2$O$_3$ and ZrO$_2$ in an amount of 5% or less.

8. An artificial dental crown comprising a glass-ceramics produced by heating glass-containing components, present within the ranges:

|  | Percent by weight |
|---|---|
| CaO | 2 to 17 |
| K$_2$O | 0.5 to 5 |
| Na$_2$O | 0.1 to 4 |
| MgO | 15 to 35 |
| SiO$_2$ | 30 to 49 |
| Al$_2$O$_3$ | 5 to 30 |

-continued

|  | Percent by weight |
|---|---|
| Fluorine (calculated as F) | 1.5 to 14 | successively at a temperature higher than its glass transition point by a range of from 10° to 100° C. and at a temperature higher than its glass transition point by a range of from 100° to 500° C., to thereby precipitate from the glass a calcium-potassium-sodium mica crystal consisting of Ca—K—Na—Mg—Al—Si—O—F and at least one crystal selected from the group consisting of an enstatite crystal, an akermanite crystal, a diopside crystal, an anorthite crystal and a richterite crystal.

9. The artificial dental crown of claim 8, wherein said glass contains at least one component selected from the group consisting of SrO, TiO$_2$, Nb$_2$O$_5$, Ta$_2$O$_5$, Y$_2$O$_3$ and ZrO$_2$ in an amount of 5% or less.

* * * * *